(12) United States Patent
Stevens et al.

(10) Patent No.: US 6,388,745 B2
(45) Date of Patent: May 14, 2002

(54) DETECTING INCLUSIONS IN TRANSPARENT SHEETS

(75) Inventors: Harrie J. Stevens, Corning; C. Charles Yu, Painted Post, both of NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/538,355

(22) Filed: Mar. 29, 2000

(51) Int. Cl.[7] .............................................. G01N 21/88
(52) U.S. Cl. .................................. 356/239.7; 356/336
(58) Field of Search .......................... 356/239.1, 239.2, 356/336, 338, 429, 430, 431; 250/559.45, 559.46, 559.47, 559.48, 559.49

(56) References Cited

U.S. PATENT DOCUMENTS

| | | | | |
|---|---|---|---|---|
| 3,361,025 A | * | 1/1968 | Gaffard | 356/239.1 |
| 3,814,946 A | * | 6/1974 | Takahashi et al. | 250/559.45 |
| 3,858,851 A | * | 1/1975 | Ogle | 356/336 |
| 4,136,961 A | | 1/1979 | Young, II | 356/239 |
| 4,571,077 A | * | 2/1986 | Skeldon | 356/239 |
| 4,623,252 A | * | 11/1986 | Hollenbeck | 356/338 |
| 5,691,811 A | | 11/1997 | Kihira | 356/237 |
| 5,859,364 A | | 1/1999 | Toda et al. | 73/105 |
| 5,894,345 A | | 4/1999 | Takamoto et al. | 356/237.1 |

\* cited by examiner

Primary Examiner—Richard A. Rosenberger
(74) Attorney, Agent, or Firm—Patrick P. Pacella; Timothy M. Schaeberle

(57) ABSTRACT

This light scattering technique for size measurement is based on the fact that an illuminated particle (inclusion) serves as a secondary radiation source in a manner which is related to its size. This technique allows for detection of inclusions in the interior of transparent solid media, such as bulk glass. When illuminated with a beam of monochromatic light such as a laser beam as the primary light source, the angular distribution of the scattered intensity originated from the inclusion in the micron to submicron range, is a function of intensity, wavelength and index of refraction. A lens and light trap block the primary light for reaching a detector. The light trap, however, allows the secondary scattered light to reach the detector.

19 Claims, 2 Drawing Sheets

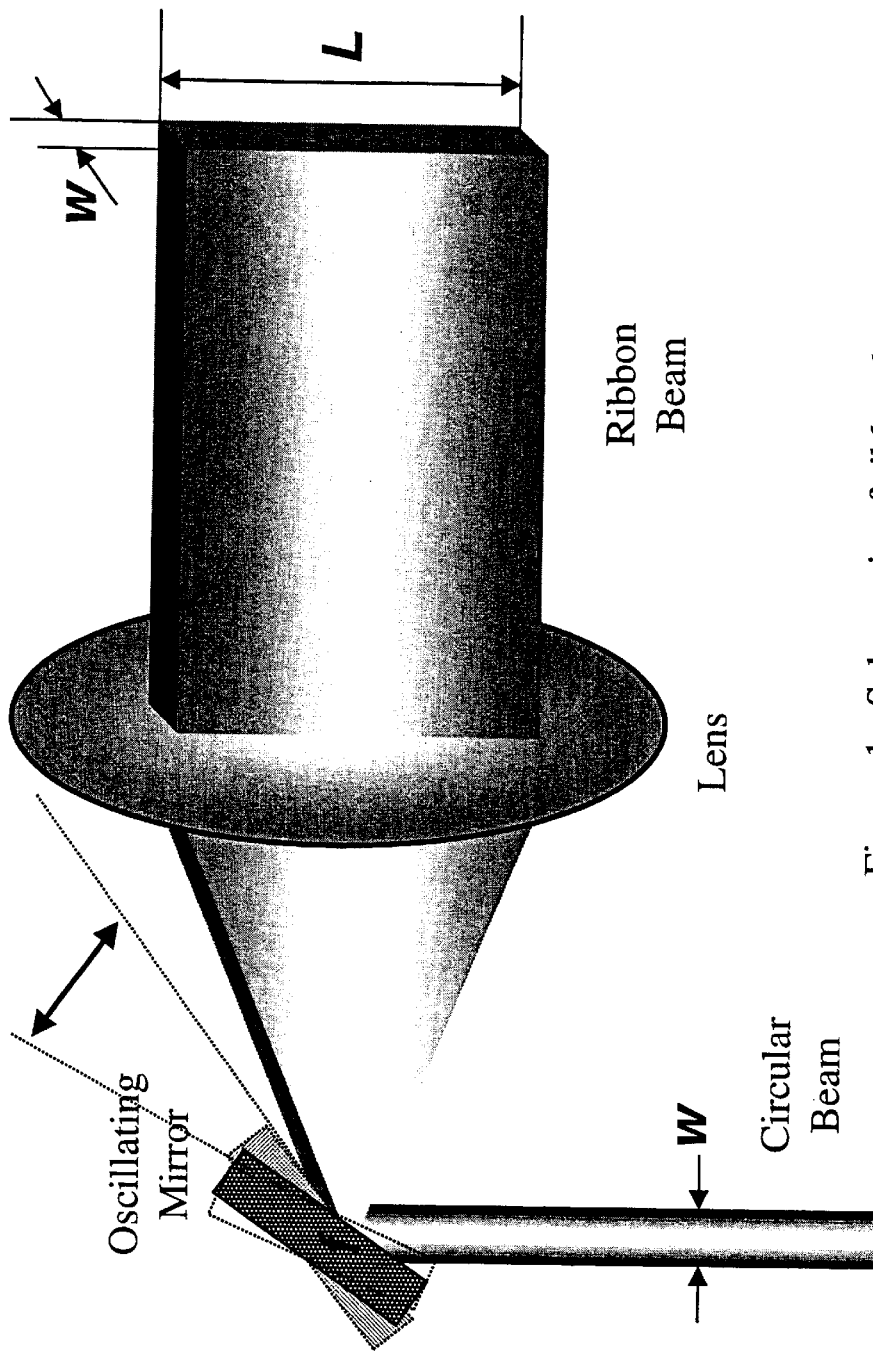
Figure 1. Schematic of ribbon beam generation.

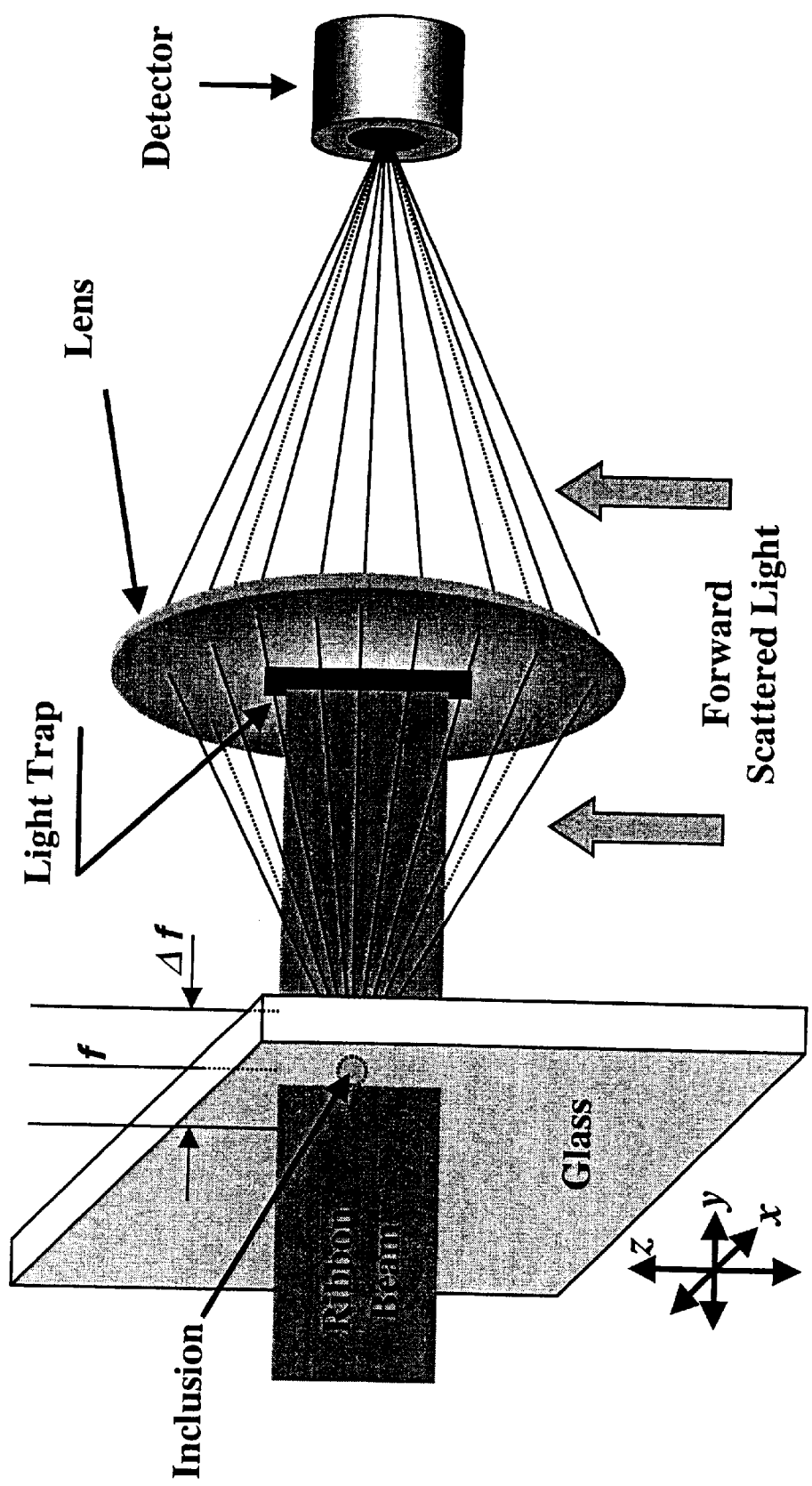
Figure 2. Schematic of glass inclusion measurement set-up.

DETECTING INCLUSIONS IN TRANSPARENT SHEETS

TECHNICAL FIELD

This invention relates to a method and instrument design for detecting small inclusions in solid media such as transparent sheets of glassy materials and plastics. Bulk glass such as high purity fused silica (HPFS®) is another example of solid media.

BACKGROUND ART

Detecting small (micron and submicron) inclusions in glass always has been a challenge. The difficulties associated with various practices are sensitivity, resolution, depth of focus, to name a few. Microscopy has the capability to detect inclusions down to the submicron range, yet it has an extremely narrow depth of focus and a small sampling area at high magnification. These are necessary for detecting small inclusions. If used alone, these restrictions make it next to impossible to analyze bulk glass. Diffused reflection/scattering has been used to identify inclusions. After mapping their location, the inclusion can be further determined by microscopy. Nevertheless, the detection limit for the diffused reflection/scattering approach is about 5 microns and as low as 1 $\mu$m. In addition, the thickness of the glass is again somewhat restricted by the narrow depth of focus of the microscopy technique.

Small particles suspended in a fluid media, such as a liquid or gas, on the other hand, can be measured routinely by light scattering techniques. The differences between inclusions in a solid glass and particles suspended in a fluid are critical. One difference is that an inclusion in a glass is stationary. Its concentration level is normally very low, thus the signal intensity is so weak that it can hardly be distinguished from noise. Noise is the cross talk between surface detection (surface signals) and in depth detection (internal signals). In addition, the location of inclusions in glass would be valuable information. Due to the dynamic nature of the suspended particles in a fluid media, their location cannot to mapped. As a result, current existing instruments are not designed with particle location mapping capability. Nevertheless, we have found that the principle behind the measurement of particles suspended in fluid media is applicable for measurement of inclusions in solid glass.

DISCLOSURE OF INVENTION

Our method and instrument design adapts the principle of light scattering to directly measure inclusion in a solid media. We redesigned the instrument intended for size measurement of particles dispersed in fluid media to achieve detection of inclusions in bulk glass. We now can map the location of inclusions in glass. The outcome is directly applicable to inclusion detection for HPFS® photomask and LCD glass.

Our light scattering technique for size measurement is based on the fact that an illuminated particle (or inclusion) serves as a secondary radiation source in a manner which is related to its size. When illuminated with a beam of monochromatic light using a laser beam as the primary light source the angular distribution of the scattered intensity originated from the inclusion in the micron to submicron range, is a function of the following: the angular distribution of the scattered intensity is a function of scattered light and the incident beam, the wavelength of the incident light, and the index of refraction of the particle relative to that of the surrounding media.

BRIEF DESCRIPTION OF THE DRAWINGS

FIG. 1 illustrates generating a collimated ribbon beam generation.

FIG. 2 illustrates the schematic of glass inclusion measurement set-up.

BEST MODE OF CARRYING OUT INVENTION

We resolved two major design issues in order to effectively adapt the light scattering technique for glass inclusion measurement. The first one is the signal intensity. The concentration level of inclusion in the glass is so low that most of the time only one inclusion at a time is in the beam path. As a result, the most common fixed angle detector arrangement (of which detector is positioned at a fix angle to the incident beam) will not be able to collect enough scattered light intensity to make it a useful signal. The second issue is the time frame for the detection cycle. The practicality of the equipment is also dictated by how long it will take to complete an inclusion inspection cycle. The following design addresses the two issues.

We achieved inclusion mapping through coordinating x-y-z movement of the glass with the signal detection. Several operating parameters have impact on inclusion mapping precision, detection sensitivity, and detection cycle time. These parameters are using a detector array or a single detector, changing width (w) and length (L) of ribbon beam, varying glass x-y-z movement speed, and using optical/electronic signal enhancing devices such as filter and chopper. Certain tradeoffs exist with each approach. The key is to find a balanced combination to achieve the objectives.

The solid media we can measure may vary widely. Generally, the solid media may be any transparent glass, plastic, crystalline material, glass-ceramic and the like. Specifically, our big challenge was measuring inclusions in high purity fused silica (HPFS®) for photomask applications. We want to detect both gaseous and refractory inclusions in the HPFS®.

The transparency of the solid media may vary widely. Obviously, if the media is too translucent, the detection system will not be accurate. We have found that the media should have an internal transparency of at least 65%. Preferably, the transparency should be at least 90%.

FIG. 1 illustrates an example of generating a collimated ribbon beam by using an oscillating mirror with the axis placed at the focal position of a convex lens. The use of a ribbon beam will greatly reduce the inspection by using an oscillating mirror with axis placed at focal position of convex lens. A laser is the preferable source for the ribbon beam generation.

FIG. 2 illustrates the schematic of glass inclusion measurement set-up. The primary (ribbon) beam is blocked by a light trap which prevents it from entering the detector. When an inclusion intercepts the incident light, it acts as a secondary radiation source. The majority of the forward scattered light, except for a small portion absorbed by the light trap, is collectively projected into the detector, which may be a photo-diode detector or a tow dimension CCD array by the lens. This greatly enhances the signal intensity. The glass is placed on the focal plane (f) of the lens, with back-and-forth movement in the x direction and stepwise motion in the z direction. If the thickness of the glass falls beyond the lens' depth of focus ($\Delta$f), an additional stepwise movement in y direction can be added for full detection coverage.

The light trap may be made of metal, plastic, alloys and the like. The light trap we used was a black anodized aluminum.

Inclusions generally are classified in two groups: solid inclusions, which are formed by bits of unmelted or foreign material; and void inclusions, commonly formed by bubbles of gas. Solid inclusions generally are formed by minute impurities in the starting materials which are fused to form a glass; bits of refractory material from the walls of the vessel in which the glass is prepared; or bits of platinum from the walls of conduits through which the glass stream flows. The solid inclusions may be opaque or clear. Void inclusions, or gas bubbles also present difficulties in visual inspection. Nonetheless, such inclusions need to be counted and properly characterized. The following Example provides an excelled technique for detecting these interior inclusions.

EXAMPLE

A boule of HPFS® is roughly in the form of a disc about 60" in diameter and varies between 6" to 10" in thickness. For making 6" size photomask substrate, for example, the 60" diameter disc is first cut into about 6¼×6¼" square blocks of full thickness of the disc. Each block is then sliced into numerous plates of about ¼" thickness. The 6¼"×6¼×¼ plates are lapped and then rough polished and subsequently feed through the inspection process.

The following is an example of our system used to detect potential inclusions in a photomask blank. One of the specifications for HPFS® fused silica to be used in photomask application is no inclusions above 2 micron (1 micron for high end applications) in size. Detection of small size inclusion in glass has always been a challenge. In one embodiment, the system consists of a 15 mW He—Ne Laser (wavelength at 633 nm), convex type lens, and a photodiode detector. The light trap is made of black anodized aluminum strip.

Inspection test result of using the prototype was very encouraging. The system showed the same, if not better, detection limit capability as that of the grid inspection approach using a microscope. Equivalent of ~2 micron size inclusion as determined has been detected. The inspection time for completing a single plate is about one minute, while it will take about one hour to accomplish the same using the microscope/grid inspection approach.

In addition to these embodiments, persons skilled in the art can see that numerous modifications and changes may be made to the above invention without departing from the intended spirit and scope thereof.

We claim:

1. An apparatus for detecting inclusions in a transparent solid media comprising in sequence:
 a light source having a primary incident beam a light;
 a solid media having at least one inclusion therein, wherein the inclusion intercepts the primary incident beam of light and creates a secondary radiation source forward scattered lights;
 a lens including a light trap; and
 a CCD array detector wherein the light trap blocks the primary beam light and prevents it from entering the detector, and wherein the lens and light trap allow a majority of the forward scattered light to protect into the detector.

2. An apparatus according to claim 1 wherein the solid media is three dimensional having an interior depth and an exterior surface, wherein the inclusion is located within the interior depth.

3. An apparatus according to claim 1 wherein the solid media is bulk glass.

4. An apparatus according to claim 1 wherein the solid media is a glassy material or plastic.

5. An apparatus according to claim 1 wherein the solid media is high purity fused silica.

6. An apparatus according to claim 1 wherein the solid media is a transparent sheet of glass.

7. An apparatus according to claim 1 wherein the primary beam of light is a laser beam.

8. An apparatus according to claim 1 wherein the lens is convex type and light trap is made of opaque material of low reflective surface.

9. An apparatus according to claim 8 wherein the low reflective surface is a black anodized aluminum.

10. An apparatus according to claim 1 wherein the detector is a two dimensional CCD array.

11. An apparatus according to claim 1 for detecting inclusions having a size in a micron or submicron range.

12. A process for detecting inclusions in a transparent solid media comprising the steps of, in sequence:
 projecting a light source having a primary incident beam of light through a solid media having at least one inclusion therein;
 intercepting the primary incident beam of light with the inclusion and creating a secondary radiation source of forward scattered light;
 projecting the primary beam of light and the secondary beam of light into a lens having a light trap;
 blocking the primary beam of light with the light trap, thereby preventing it from entering a CCD detector; and
 projecting a majority of the forward scattered light through the light trap into the detector.

13. A process according to claim 12 wherein the solid media is three dimensional having an interior depth and an exterior surface, wherein the inclusion is located within the interior depth.

14. A process according to claim 12 wherein the solid media is bulk glass.

15. A process according to claim 12 wherein the solid media is a glassy material or plastic.

16. A process according to claim 12 wherein the solid media is high purity fused silica.

17. A process according to claim 12 wherein the solid media is a transparent sheet of glass.

18. A process according to claim 12 wherein the primary beam of light is a laser beam.

19. A process according to claim 12 for detecting inclusions having a size in a micron or submicron range.

* * * * *